(12) United States Patent
Harris et al.

(10) Patent No.: US 8,984,674 B1
(45) Date of Patent: Mar. 24, 2015

(54) TRAINING URINAL ATTACHMENT FOR CONVENTIONAL TOILETS

(71) Applicants: Charles Edward Harris, Anacortes, WA (US); Charles David Harris, Anacortes, WA (US)

(72) Inventors: Charles Edward Harris, Anacortes, WA (US); Charles David Harris, Anacortes, WA (US)

( * ) Notice: Subject to any disclaimer, the term of this patent is extended or adjusted under 35 U.S.C. 154(b) by 80 days.

(21) Appl. No.: 13/987,752

(22) Filed: Aug. 27, 2013

Related U.S. Application Data (60) Provisional application No. 61/743,624, filed on Sep. 7, 2012.

(51) Int. Cl.
  *E03D 9/00* (2006.01)
  *A61F 5/451* (2006.01)
(52) U.S. Cl.
  CPC ... *A61F 5/451* (2013.01); *Y10S 4/05* (2013.01)
  USPC .............. 4/300.3; 4/144.1; 4/144.4; 4/DIG. 5
(58) Field of Classification Search
  USPC ................ 4/300.3, DIG. 5, 144.1, 144.4, 902
  See application file for complete search history.

(56) References Cited

U.S. PATENT DOCUMENTS

| | | | |
|---|---|---|---|
| 2,791,780 A | 5/1957 | Krischer |
| 2,980,919 A | 4/1961 | Otto et al. |
| 3,071,778 A | 1/1963 | Renshaw |
| 3,193,845 A | 7/1965 | Funk |
| 3,914,803 A | 10/1975 | Gregovski |
| 4,060,859 A | 12/1977 | Anderson |
| 4,348,776 A | 9/1982 | Sarjeant |
| 4,612,676 A | 9/1986 | Whitman |
| 5,148,553 A | 9/1992 | Jermann |
| 5,564,135 A | 10/1996 | Jones et al. |
| 6,385,785 B1 | 5/2002 | Linden |
| 6,938,278 B2 | 9/2005 | Parks et al. |
| 7,043,773 B2 | 5/2006 | McAleenan, Jr. |
| 7,178,177 B1 | 2/2007 | Valencia |

*Primary Examiner* — Tuan N Nguyen
(74) *Attorney, Agent, or Firm* — Todd N. Hathaway (57) ABSTRACT

A training urinal attachment mountable to the bowl of a toilet. The attachment includes a resiliently collapsible shell having an intake opening that receives a flow of urine from a standing child and a discharge opening that directs the flow into a collection area of the bowl. The shell is mounted on the rim of the bowl in an area that is covered by the seat of the toilet when lowered. When the seat is lowered, the shell compresses to a collapsed configuration in the area between the seat and the rim. When the seat is raised, the shell expands to an erected configuration in which the intake opening extends above the rim to receive the flow of urine. The discharge opening is visible through the intake opening to provide the child with a target to aid in training.

20 Claims, 6 Drawing Sheets

TRAINING URINAL ATTACHMENT FOR CONVENTIONAL TOILETS

RELATED APPLICATIONS

This application claims the benefit of U.S. Provisional Patent Application Ser. No. 61/743,624 filed Sep. 7, 2012.

BACKGROUND a. Field of the Invention

The present invention relates generally to toilets, and, more particularly, a urinal attachment that is mountable to the bowl of the conventional toilet as an aid in toilet training of young male children.

b. Related Art

Toilet training of young male children presents certain challenges. For the most part, young boys quite willingly embrace the concept of urinating while standing, however their ability to maintain a proper aim is slower to develop. The results, well known to parents, is that the full stream may not enter the bowl, and a portion thereof may therefore come to reside on the rim or sides of the bowl, or on the adjoining floor, walls, or on a variety of other surfaces. Many of these areas are difficult to access, rendering an unwelcome cleaning chore even less pleasant, but if not tended to the situation quickly becomes unsanitary and malodorous.

The difficulties described in the preceding paragraph are of an age-old nature, consequently numerous efforts have been made at improving the situation. In the modern era many of these efforts have taken the form of splash guards and/or miniature urinals that are mountable to conventional household toilets (e.g., Western-type flush toilets), either temporarily or more-or-less permanently. In general such devices comprise surfaces that are intended to capture and direct the flow into the bowl and prevent "splatters" from escaping into the adjoining area, but for the most part they have suffered from various deficiencies that have rendered them less than entirely satisfactory.

For example, some of these devices have consisted of channels or shields formed of plastic or other rigid material that temporarily "clip" or otherwise attach to the rim of the bowl for use. A distinct disadvantage is that these types of devices generally obstruct/block the seat from being lowered, or otherwise interfere with the toilet being used in the seated position, such that the devices must generally be removed from the toilet except at times when their services are specifically required; this need to repeatedly mount and remove the attachment, over and over again, can quickly become tedious for the parent, and moreover the time required to do so can be present a significant problem when the needs of nature are urgent.

Some devices have to one extent or another avoided the problem of blocking the toilet seat, but at the expense of other drawbacks. For example, devices have been proposed that include wing-like walls that depend from the seat so as to form a shield when the latter is raised, while others have employed bellows-like or telescoping structures mounted to the seat, either directly or indirectly using linkages, so as to be deployed along the sides of the bowl as the seat is raised. As a group, such devices are cumbersome and may be inconvenient or difficult for some users. They also tend to provide poor protection against misdirected flow and spray, in some cases due to gaps and openings inherent in the designs, and also feature large and/or complexly shaped surfaces that are very difficult to clean. In addition, both the complexity, size and materials employed tend to render such devices both expensive to manufacture and vulnerable to wear and damage in use.

Another group of devices consists of temporary urinals that hang on or otherwise mount externally to the bowl of the toilet and include their own collection reservoirs; while some of these may be configured to avoid interference with lowering the seat, these devices present their own problems of having to repeatedly remove the collection vessel and dump its contents into the toilet bowl, followed by a rinsing if an odor is to be avoided, and moreover they are by nature both physically and aesthetically obtrusive.

Yet another drawback, shared by many of the devices of the types described above, is that even when the device is installed/erected a significant portion of the rim of the bowl is left exposed, leaving this area needing to be cleaned and also creating the opportunity for leakage along the rim.

Accordingly, there exists a need for an apparatus that is mountable to a conventional toilet for capturing and directing a flow of urine from a standing male child into a bowl of the toilet, that when attached to the toilet does not block or otherwise interfere with use of the seat of the toilet. Furthermore, there exists a need for such an apparatus that is effective in capturing and directing the flow and associated spray, but without large or convoluted surfaces that are difficult to clean. Still further, there exists a need for such an apparatus that is compact and not bulky, and is not physically or visually obtrusive. Still further, there exists a need for such an apparatus that minimizes the opportunities for escape or leakage from the flow of urine captured thereby. Still further, there exists a need for such an apparatus that can be economically manufactured while remaining adequately durable and long-lasting in use.

SUMMARY OF THE INVENTION

The present invention addresses the problems cited above, and is a training urinal attachment that is mountable at the rim of a toilet bowl and that is collapsible in response to the seat of the toilet being lowered thereon.

In a broad aspect, the present invention provides a training urinal that is attachable to a bowl of a toilet, the training urinal comprising: (a) a resiliently collapsible shell, comprising an intake opening that receives a flow of urine from a standing child, a discharge opening that directs the flow of urine into a collection area of a bowl of a toilet, and a passage that constrains the flow of urine from the intake opening to the discharge opening; and (b) a mounting portion attachable to the toilet so as to position the collapsible shell over an area of a rim of the bowl that is covered by a seat of the toilet when lowered; (c) whereby in response to the seat of the toilet being lowered the shell of the urinal attachment compresses to a collapsed configuration between a lower side of the seat and an upper side of the rim of the bowl, and in response to the seat being raised the shell expands to an erected configuration in which the intake opening extends upwardly above the rim of the toilet to receive a flow of urine from a standing child.

The resiliently collapsible shell of the training urinal attachment may comprise a shell molded of a resiliently flexible material. The shell may be unitarily molded of the resiliently flexible material.

The passage of the resiliently collapsible shell may comprise an inwardly and downwardly angled passage that directs the flow of urine therethrough towards the bowl of the toilet. The resiliently collapsible shell may comprise a generally down-curved shell having the inwardly and downwardly angled passage therein. The intake openings and discharge opening may be aligned along a line of sight through the inwardly and downwardly angled passage so that the discharge opening is visible through the intake opening for use as a target by a standing child. The downwardly angled passage may comprise a curved passage that tapers from larger to smaller from the intake opening to the discharge opening. The down-curved shell may have a horizontal length approximately equal to or less than a predetermined width of a ring of the seat of the toilet, so that the shell is substantially covered by the ring when the seat is lowered.

The resiliently collapsible shell may further comprise an inwardly raised lip extending over at least a lower portion of a perimeter of the intake opening that forms a dam against backflow from the flow of urine escaping the intake opening. The discharge opening may comprise an opening having a raised upper edge that provides an enlarged view into the collection area of the bowl that is visible through the intake opening. The resiliently collapsible shell may further comprise a hood portion extending above the intake opening that substantially covers the intake opening when the shell is in the collapsed configuration with the seat of the toilet lowered thereon.

The mounting portion attachable to the toilet may comprise means for detachably mounting the shell to a rim of the bowl of the toilet. The means for detachably mounting the shell to the rim of the bowl of the toilet may be selected from the group consisting of suction cups, brackets, clips, magnets, adhesives, and combinations thereof. The mounting portion attachable to the bowl of the toilet may comprise at least one suction cup mounted to the resiliently collapsible shell that is attachable to the rim of the bowl of the toilet. The at least one suction cup may comprise first and second suction cups mounted to a lower side of the resiliently collapsible shell proximate the intake and discharge openings and facing towards one another, that engage outer and inner vertical sides of the rim of the bowl of the toilet. The resiliently collapsible shell may further comprise a depending flange portion extending downwardly proximate the intake opening so as to be located adjacent the outer vertical side of the rim of the bowl, the depending flange having the first suction cup mounted thereon, and a lower side wall portion extending downwardly proximate the discharge opening so as to be located adjacent the inner vertical side of the rim of the bowl, the lower side wall portion having the second suction cup mounted thereon. The shell may further comprise a horizontally flattened bottom wall portion located intermediate the depending flange portion and the lower side portion, that rests atop a horizontal upper side of the rim of the bowl of the toilet so as to support and stabilize the shell on the rim.

In a particular aspect, the invention provides a training urinal attachment mountable to a bowl of a toilet, the training urinal attachment comprising: (a) a generally down-curved resiliently collapsible shell formed of a resiliently flexible material having a memory shape, the resiliently collapsible shell comprising: (i) an intake opening that receives a flow of urine from a standing child; (ii) a discharge opening that directs the flow of urine into a collection area of a bowl of the toilet; and (iii) a tapered passage that constrains the flow of urine from the intake opening to the discharge opening; (iv) the intake and discharge openings lying along a common line of sight extending at an inward and downward angle through the passage so that the discharge opening is visible through the intake opening for use as a target by a standing child; (b) at least first and second suction cups mounted to a lower side of the resiliently collapsible shell proximate the intake and discharge openings and facing towards one another, that engage inner and outer vertical sides of a rim of the bowl of the toilet so as to detachably mount the resiliently collapsible shell thereto; and (c) a horizontally flattened bottom wall portion located intermediate the intake opening and the discharge opening, that rests atop a horizontal upper side of the rim of the bowl of the toilet so as to locate and stabilize the shell thereon; (d) whereby, in response to the seat of the toilet being lowered the shell of the urinal attachment compresses to a collapsed configuration between a lower side of the seat and an upper side of the rim of the bowl, and in response to the seat being raised the shell expands to an erected configuration in which the intake opening extends upwardly above the rim of the toilet to receive a flow of urine from a standing child.

The present invention further provides a method for training a standing child to urinate into a toilet, comprising the steps of: (a) providing a resiliently collapsible shell comprising an intake opening that receives a flow of urine from a standing child, a discharge opening that directs the flow of urine into a collection area of a bowl of the toilet, and passage that constrains the flow of urine from the intake opening to the discharge opening; (b) mounting the resiliently collapsible shell to the toilet so that the shell is positioned over an area of a rim of the bowl that is covered by a seat of the toilet when lowered; (c) lowering the seat of the toilet to the rim of the bowl so that the seat compresses the resiliently collapsible shell to a collapsed configuration in an area between a lower side of the seat and an upper side of the rim of the bowl; and (d) raising the seat of the toilet away from the rim of the bowl so that the resiliently collapsible shell expands to an erected configuration in which the intake opening extends upwardly above the rim to receive the flow of urine from a standing child. The method may further comprise the step of aligning the intake opening and the discharge opening along a common line of sight extending at an inward and downward angle through the passage of the resiliently collapsible shell, so that when the shell is in the erected configuration the discharge opening is visible through the intake opening for use as a target by a standing child.

These and other features and advantages of the invention may be more fully appreciated from a reading of the following detailed description with reference to the accompanying drawings.

DETAILED DESCRIPTION

Figure 1:
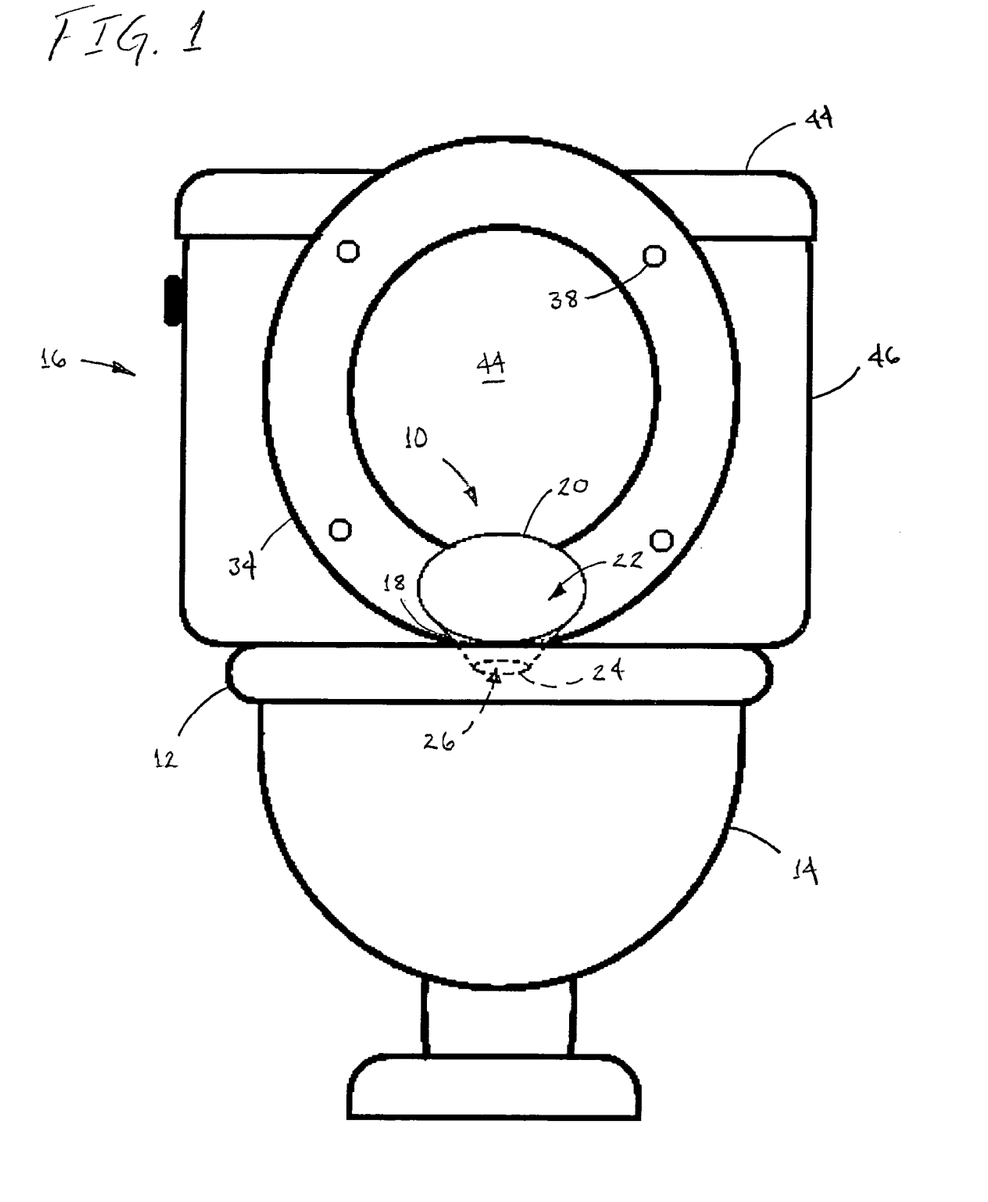
FIG. 1 is a front elevational view of a resiliently collapsible training urinal attachment in accordance with the present invention mounted to a bowl of an exemplary conventional flush toilet.

FIG. 1 shows a training urinal attachment 10 in accordance with the present invention, mounted to the rim 12 of the bowl 14 of a conventional flush toilet 16. As will be described in greater detail below, the urinal attachment 10 is formed in whole or in part of a resiliently flexible material that allows it to transition between a collapsed form and the erected form that is shown, in FIG. 1.

As can be seen, urinal attachment 10 includes a generally tubular shell having a first end 20 with an intake opening 22 and a second end 24 with a discharge opening 26. In the embodiment that is illustrated, the urinal shell is tapered so as to have a somewhat conical or funnel-shaped form, with the generally circular intake opening being sized substantially larger than the outlet opening; this configuration provides several advantages in terms of collection and direction of the flow, as will be described in greater detail below, however it will be understood that in some embodiments of the invention the tubular shell of the urinal may have other shapes (e.g., rectilinear or vertically/horizontally flattened oval or ovoid cross sections; greater/lesser or reverse tapers; differently shaped or directed openings).

Figures 2A, 2B:
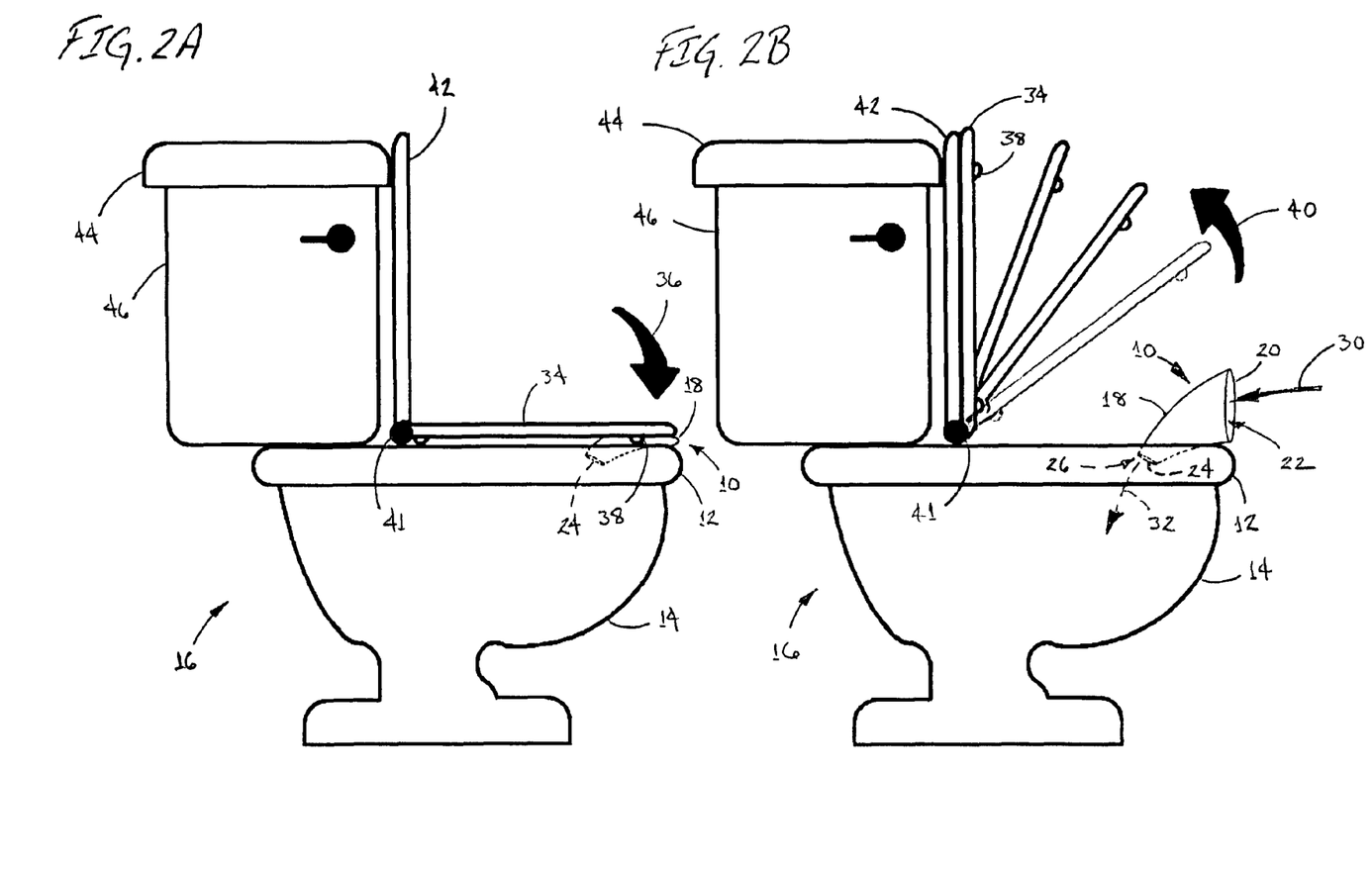
FIGS. 2A and 2B are first and second side elevational views of the training urinal and toilet assemblage of FIG. 1, showing respectively the manner in which the collapsible training urinal attachment is resiliently compressed beneath the toilet seat when lowered so as to permit unencumbered use of the latter, and the manner in which the urinal attachment resiliently expands as the toilet seat is lifted so as to assume a generally conical form for capturing and directing a flow of urine into the bowl of a toilet.

As can be seen in FIG. 1 and also FIG. 2B, the urinal attachment 10 is preferably mounted such that the intake opening 22 is located proximate the rim 12 of the toilet bowl, with the lower edge of the intake opening being positioned adjacent the upper-outer edge of the toilet rim and extending upwardly therefrom. As noted above, the end 20 of the urinal attachment and intake opening 22 are generally circular in the embodiment that is shown, however, in some embodiments the lower edge of the opening may be flattened or provided with a rim or lip that conforms generally with the upper surface of the rim 12 of the bowl so as to create a more complete seal therewith; in addition, a raised lip, flange or other barrier may be formed along the lower edge of the intake opening 22, so as to form a "dam" against urine running back out the intake opening.

Thus positioned, the intake opening 22 of urinal attachment 10 is located at an elevation generally optimal to receive a flow of urine from a standing male child, entering in the direction indicated by arrow 30 in FIG. 2B, the comparatively large size of the intake opening serving to capture the flow despite the unavoidable variations in direction. Furthermore, the child may stand close to the toilet so that the flow enters the urinal attachment more-or-less directly, or, with improvement in aim, may step back a bit and use the intake opening more as a target.

After entering the urinal attachment the flow is constrained by the wall or walls of shell 18, and directed inwardly and outwardly to the discharge opening 26, from which the flow exits towards the collection area of the bowl 14 in the direction indicated by arrow 32. In the illustrated embodiment, the conical/funnel-shaped shell 18 of the attachment has a down-curved configuration, such that when mounted to a toilet the intake opening is upright and extends around a more-or-less horizontal axis to receive a flow traveling in a corresponding direction, while the discharge opening is formed around an axis angled in a downward direction; as opposed to a more straight-line configuration, the down-curved shell provides the combined advantages of angling the discharge flow more directly towards the capture area of the bowl while keeping the length of the shell relatively short in the horizontal direction so that it will fit generally beneath the surround of the toilet seat without protruding excessively, as will be described in greater detail below.

The training urinal attachment may be mounted to the toilet by any of a number of suitable mechanisms, so long as the urinal attachment is oriented to receive/discharge the flow as described above and also is located along the rim of the bowl in the area beneath the seat when lowered. For example, the embodiment that is illustrated in FIGS. 1 and 2A-2B may suitably be mounted to the rim of the bowl using an adhesive (e.g., an adhesive layer, glue, adhesive tape), preferably one having sufficient strength to hold the urinal attachment in place throughout the desired period of installation, yet which allows the attachment to be separated from the rim when desired (e.g., by pulling or cutting), with any residue being removable by use of solvents, scrubbing, or other comparatively convenient techniques. Examples of other mechanisms by which the urinal attachment may be mounted to the toilet bowl include suitably configured brackets, clips, suction cups and magnets. In those embodiments that employ a detachable mounting, the shell may be provided with a tab, flap or other structure to provide a convenient, sanitary way to remove the device for cleaning. The interior of the shell can also be cleaned while remaining attached to the bowl, by spraying a disinfectant or other liquid cleanser through the intake opening so that the liquid flows through the shell and drains into the bowl.

FIGS. 2A-2B illustrate the manner in which the training urinal attachment cooperates with the seat of a conventional toilet to permit the latter to be used without impairment while the urinal attachment remains mounted to the toilet.

As was noted above, and as can be seen in FIGS. 2A-2B, the training urinal attachment mounts at the rim 12 of the toilet bowl 14, so as to be "sandwiched" between the rim and the seat when the latter is in the lowered position. As was also noted above, the shell 18 of the urinal attachment is formed of a resiliently flexible material. Thus, as is illustrated in FIG. 2A, when the seat 34 of the toilet is lowered, in the direction indicated by arrow 36, the underside of the seat ring contacts the shell 18 of the urinal attachment and presses it downwardly towards the upper surface of rim 12, causing the shell of the urinal attachment to collapse progressively and resiliently between the two. Stops 38 are conventionally installed on the undersides of toilet seats to prevent the lower surface of the seat resting directly atop the rim 12; these bear the weight of a person resting on the seat and form a gap of a minimum height, the thickness and/or material characteristics of the shell preferably being selected to allow it to fit into the gap when collapsed without being excessively crushed/damaged.

Thus, in the collapsed configuration shown in FIG. 2A, the urinal attachment does not obstruct or otherwise interfere with normal use of the toilet with the seat in the lowered position. As noted above, because of the preferred embodiment's short length in the horizontal plane, the inward/discharge end of the shell does not protrude a significant distance into the open area of the seat within the ring and thus avoids presenting an obstacle to urination when in a seated position; as an additional protection, some embodiments may include a raised flange or other feature that acts as a "dam" against urine flowing forwardly on the sides of the shell in the event of it being impinged by a misdirected flow. Moreover, a dam or other shield may be included to prevent a child from urinating between the toilet rim and seat, or urinating above the toilet seat, when in a seated position.

In order to use the training urinal attachment, the seat of the toilet is raised in a conventional manner, as indicated by arrow 40 in FIG. 2B, the seat pivoting about hinge 41 and typically coming to rest, together with lid 42 when present, against the cover 44 of the tank 46. In so doing, the shell 18 of the urinal attachment is released from the compression exerted by the seat, so that the memory of the resiliently flexible material causes the shell to expand to the erected configuration shown in FIG. 2B. The urinal attachment 10 is thus quickly and conveniently readied for use, i.e., to receive a flow of urine in the direction indicated by arrow 30 as described above.

Figure 3:
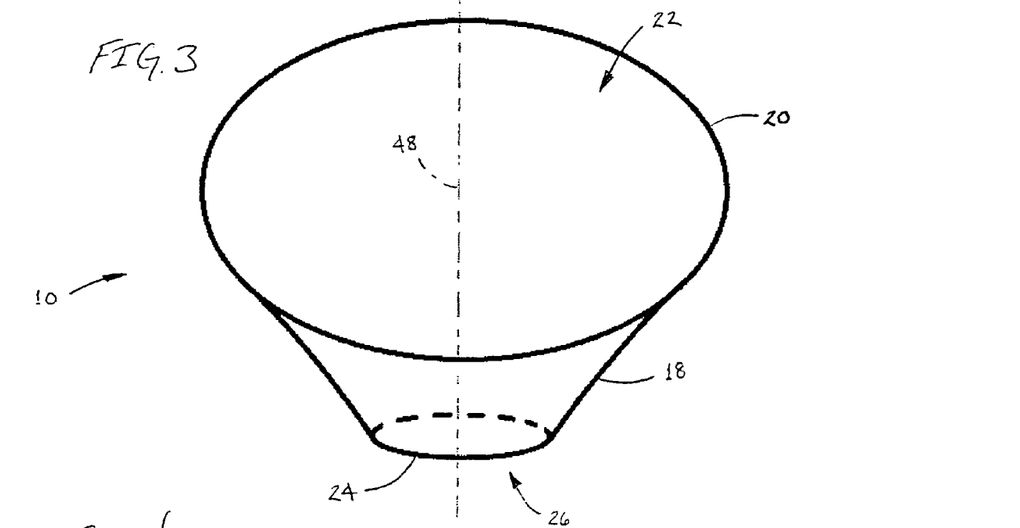
FIG. 3 is a front elevational view of the training urinal attachment of FIGS. 1-2B, showing the generally conical configuration and also the entrance opening thereof in greater detail.

FIGS. 3-6 show the structure of the shell of urinal attachment 10 in greater detail. As was noted above, the shell 18 is formed of a resiliently flexible material, such as silicone, urethane, PVC or other resilient natural or synthetic rubber or plastic, with the strength/durometer of the material and/or the thickness of the wall being selected such that the shell will collapse resiliently under the downward force exerted by the seat at a spaced distance from the hinge 42, preferably proximate the front of the bowl 14 and opposite tank 46, and will return to substantially its original shape when released. The resiliently collapsible construction of the shell obviates the need for complicated, difficult to clean, wear-prone mechanisms such as employed by some prior devices. In the illustrated embodiment, shell 18 is a unitary, one-piece member, molded or otherwise formed of the resiliently flexible material, greatly facilitating economical manufacture. Furthermore, as can be seen in FIG. 3, the surfaces of the shell, particularly on the inside, are preferably smooth and unbroken, which not only facilitates flow through the interior and reduces spatter, but also greater facilitates cleaning of the article. The one-piece flexible structure therefore provides significant advantages, however, it will be understood that in some instances the shell may be made using multiple-part construction.

Figure 4:
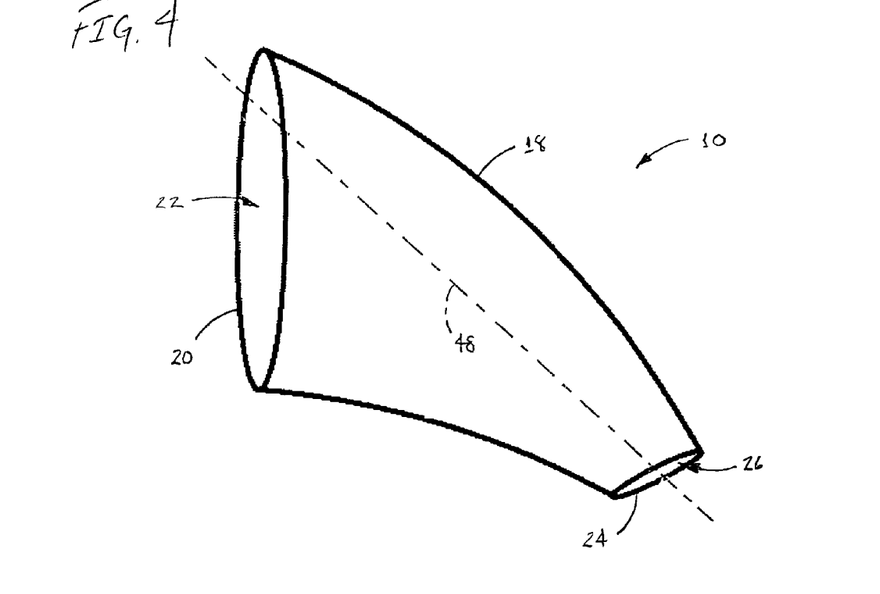
FIG. 4 is a right side elevational view of the training urinal attachment of FIG. 3, showing in greater detail the tapering and downwardly curved configuration of the conical form of the attachment and also the discharge opening through which the flow of urine exits in a generally downward path towards the collection area of the bowl of the toilet.
Figure 5:
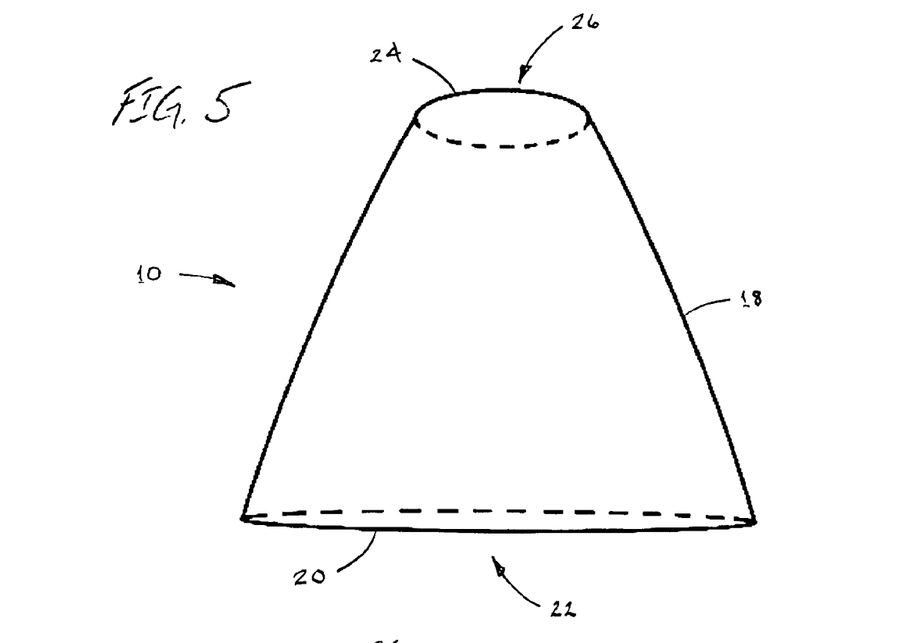
FIG. 5 is a top plan view of the training urinal attachment of FIGS. 3-4, showing in greater detail the relationship between the intake and discharge openings thereof.
Figure 6:
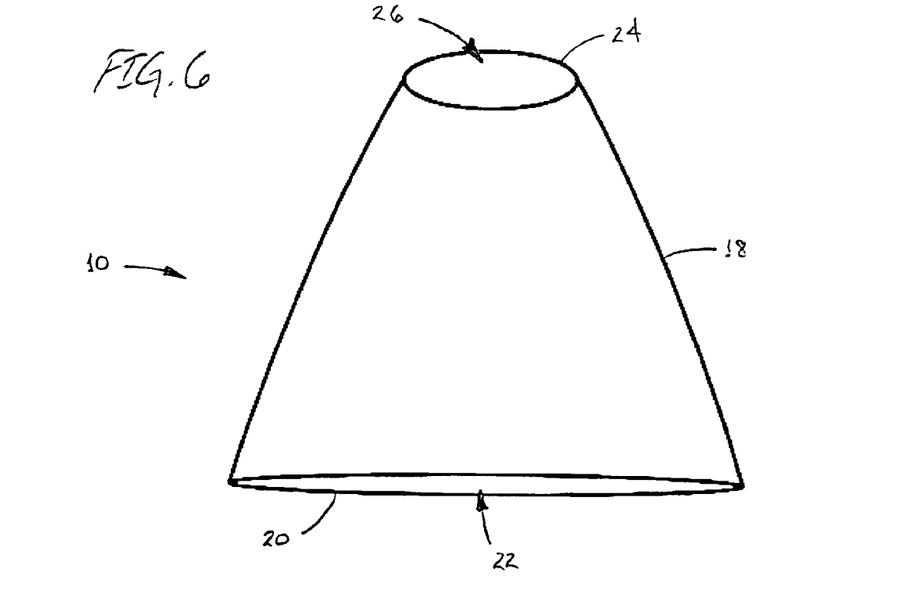
FIG. 6 is a bottom plan view of the training urinal attachment of FIGS. 3-5, again illustrating the relationship between the intake and discharge openings of the attachment.

FIGS. 4-6 further illustrate the configuration of shell 18 and the relationship between the intake and discharge openings 22, 26. As was noted above, the shell in the illustrated embodiment has a somewhat funnel-like or conical shape that is generally down-curved, with the wall of the shell being somewhat longer on the upper side and shorter on the lower, with the main plane of the intake opening extending generally vertically when mounted on the toilet and that of the discharge opening lying more horizontal so that the flow exits towards the containment area of the bowl. As was also described, this configuration provides the dual advantages of efficiently capturing and directing the flow while being somewhat shortened in the horizontal plane, so as to fit under the ring of the toilet seat without projecting significantly into the open area in the middle. However, while the shell of urinal attachment 10 thus follows a generally curved axis, the shell is also preferably configured such that the discharge opening remains visible to view through the intake opening at the other end; as can be seen in FIGS. 3-4, a line of sight 48 preferably extends at an inward and downward angle from the intake opening 22 to the discharge opening 24, such that the discharge opening will be visible to a child standing proximate the toilet. This permits the child to use the discharge opening as a "target" to improve his aim, thus advancing the purpose of the device as a temporary training aid rather than a permanent fixture.

Figure 7:
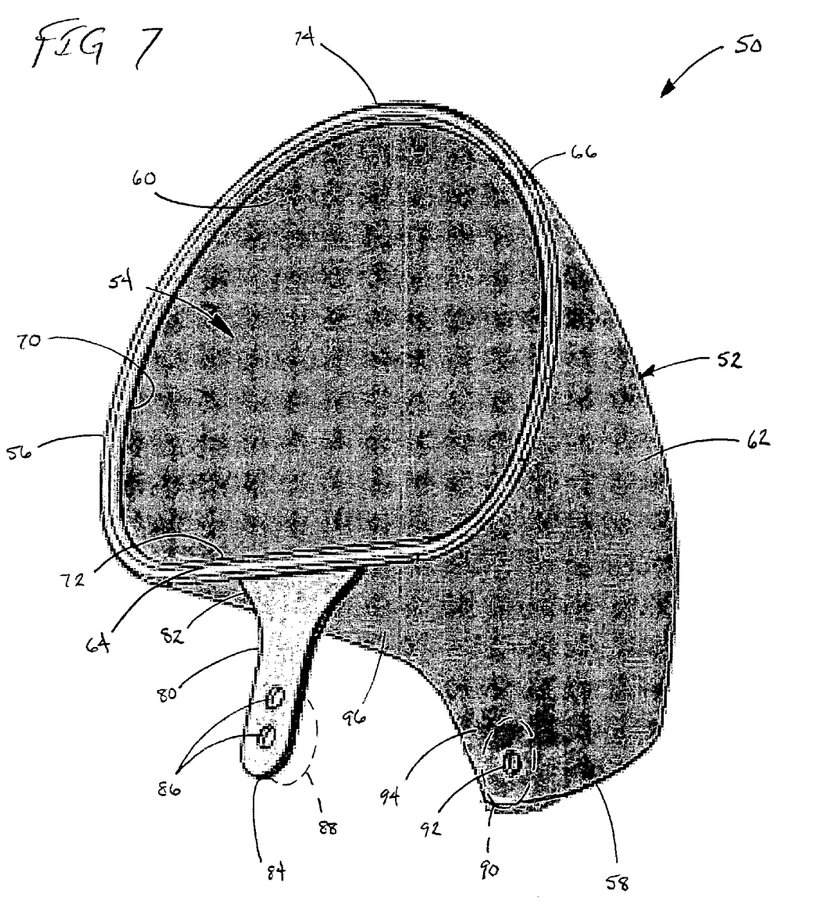
FIG. 7 is a lower perspective view of another resiliently collapsible training urinal attachment in accordance with the present invention, that is attachable to the rim of a conventional toilet by suction cups installed in downward projections from the shell of the attachment.

FIG. 7 shows another example of a training urinal attachment in accordance with the present invention. Similar to the embodiment described above, the training urinal attachment 50 shown in FIG. 7 includes a down-curved, resiliently collapsible, relatively thin-walled shell 52, suitably formed of molded silicone, polyurethane or other resilient material, having sufficient flexibility to collapse under the weight of the toilet seat without undue resistance. The hollow interior of shell 52 defines a correspondingly down-curved passage 54 that constrains the flow of urine and directs it from the intake opening 56 at one end of the shell to the discharge opening 58 at the other, the latter being angled to direct the discharge towards the collection area of the toilet bowl. The flexible shell preferably has a smooth, slick surface 60 on the interior for enhanced flow and cleanliness, and a somewhat roughened otherwise textured surface 62 on the exterior to aid in gripping and handling the attachment, e.g., during installation/removal and cleaning.

As can be seen with further reference to FIG. 7, the intake opening 56 of shell 52 differs somewhat from that of the embodiment described above, having a generally flat, horizontal lower edge portion 64 that conforms to the flat, horizontal upper surface of the rim of the bowl when the urinal assembly is mounted thereon. Above the lower edge portion, the upper portion 66 of the opening is in the form of a rounded arch, extending upwardly above the rim of the bowl when the shell is in its released, erected configuration. An inwardly projecting lip 70 extends about the inside perimeter of the intake opening, molded integrally with the remainder of the shell, providing additional support to help maintain the opening upright in the erected configuration and also reducing the opportunity for tearing or other damage to the edge of the shell. Along the lower portion of the perimeter the upstanding lip forms a dam 72, that extends somewhat parallel to the rim of the toilet when installed and that acts as a dam to help prevent backflow from the stream exiting the entrance opening during use. The upper arch portion of the lip, together with the adjoining material of the upper part of the shell, in turn forms a hood that extends down to cover and substantially enclose the opening into the urinal attachment when the shell is collapsed under the toilet seat, providing both aesthetic and sanitary benefits. As can better be seen in FIG. 8C, lip 70 is preferably formed with smoothly radiused upper and lower edges 76, 78.

As can be seen with further reference to FIG. 7, a mounting flange 80 extends downwardly from the lower side of shell 52, below intake opening 54. The upper end of the flange is joined at its base 82 to the lower portion of lip 70 of the urinal shell, the base 82 being flared outwardly to increase the length of the joint with the lip and therefore the strength of the connection. The lower end of the flange in turn forms a depending tap 84, that permits the flange to be gripped between the fingers of a hand, e.g., to be pulled downwardly during installation. First and second vertically spaced openings 86 are formed through the mounting flange above lower end 84, that provide alternate positions for a front suction cup 88: suction cup 88 is suitably a conventional, "off-the-shelf" molded plastic suction cup capable of holding against the surface of the toilet, having a base plug sized to be pressed therethrough either of the holes 86 in the resilient material of flange 80 so as to retain the suction cup thereon.

With the urinal attachment placed atop the rim of the bowl of the toilet, flange 80 depends just outside the rim of the bowl, so that first suction cup is positioned closely adjacent and facing the generally vertical surface of the outer wall of the rim. A second, corresponding suction cup 90 is retained in an opening 92 formed through a depending lower wall portion 94 of shell 52, facing opposite and towards first suction cup 88. With the urinal attachment located atop the rim of a toilet bowl, the downwardly angled lower wall portion of the shell extends closely inside the edge of the rim, so that second suction cup is positioned closely adjacent the generally vertical surface of the inside wall of the rim.

A substantially flat, horizontal lower wall portion 96 of the shell extends rearwardly from the intake opening 54, so as to be positioned intermediate mounting flange 80 and downwardly-extending wall portion 94. The horizontal lower wall portion provides a broad contact surface that engages the corresponding flat, horizontal upper surface of the rim of a toilet bowl so as to stabilize the shell and the rest of the urinal attachment in its intended orientation. Openings 86, 92 are spaced below horizontal wall 96 by a distance selected such that the suction cups mounted therein will be held adjacent the inner and outer walls of the rim and not below, for the majority of bowls, and also preferably so that the suction cups will be generally level with one another.

The above-described relationship, between the lower wall of the shell and the locations of the suctions cups, enables the urinal attachment to be mounted to the bowl of a toilet in a quick and convenient manner by simply setting the lower wall 96 of the shell atop the rim of the bowl, with the intake opening facing outwardly, then pressing the suction cups together, for example, by reaching through the opening with one or more fingers and pressing with the thumb (or other fingers) against the mounting flange on the outside. The multiple, vertically-spaced openings 86 in the mounting flange allow the level of the suction cups to be adjusted to accommodate rims having different heights; similarly, as can best be seen in FIG. 8B, mounting flange 80 and wall 94 are preferably angled apart slightly (e.g., 10-15°) when in the relaxed, uninstalled configuration, so as to be able to accommodate differing widths (thicknesses) of rims when pressed together. When desired, the suction cups are easily detached from the rim of the bowl to permit removal of the urinal attachment (e.g., for cleaning), after which the urinal attachment may be installed again in the manner described above.

As can be seen with further reference again to FIG. 8B, the discharge opening 58 in the illustrated embodiment is formed as a section through the down-curved inner end of shell 52. The main plane of the discharge opening is preferably angled upwardly towards the center of the bowl, so that the forward edge 100 (i.e., the edge towards the outside of the toilet) of the opening is relatively depressed and the upper, rearward edge 102 is comparatively raised, preferably to a level approximately even with the lower side 96 of the shell and consequently approximately level with the top of the rim when installed on a bowl. The forward/lower edge 100 of the discharge opening thus extends to a level below the lower wall 96 of the shell, so as to contain the flow of urine to a point below the rim of the bowl before it is discharged through opening 58. The raised rearward/upper edge 102 of the opening is in turn elevated above the inwardly and downwardly angled line of sight 104 through the passage of the shell, providing an enlarged view of the bowl through opening 54 that can be employed by the child as a "target" to help develop aim while using the urinal attachment.

Figure 8A:
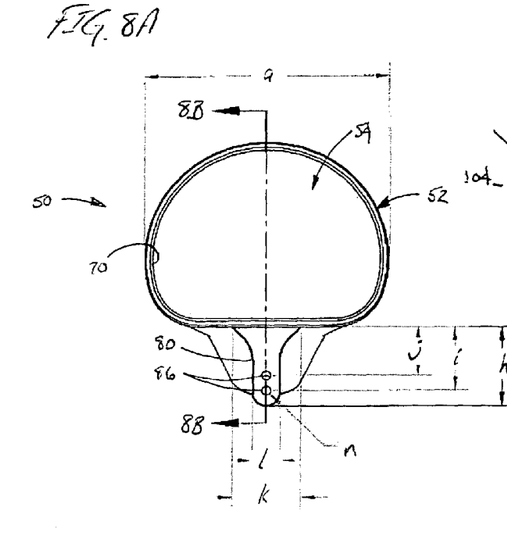
FIG. 8A is a front elevational view of the training urinal attachment of FIG. 7.
Figure 8B:
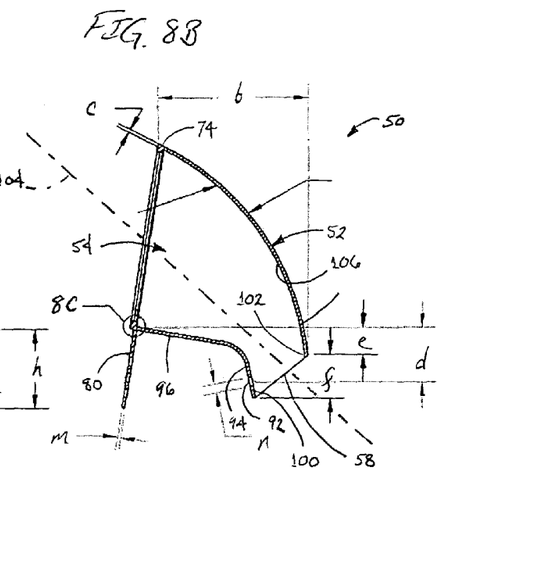
FIG. 8B is a cross-sectional view of the training urinal attachment of FIG. 7, taken along line 8B-8B in FIG. 8A, showing the configuration of the shell and the mounting portions of the attachment in greater detail.

The inside upper surface 106 of the urinal shell is preferably concavely down-curved as shown in FIG. 8B, so that the flow of urine, whether impacting the surface directly or after contacting the lower surfaces of the shell, is guided smoothly into the bowl of the toilet with a minimum of splashing or backflow. As noted above, the interior surface of the shell preferably has a smooth, slick surface, to drain cleanly and minimize the accumulation of urine.

Figure 8C:
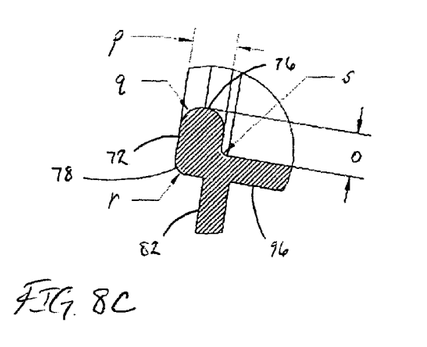
FIG. 8C is an detail cross-sectional view of the lower rim of the training urinal attachment of FIG. 7, of the area indicated at 8C in FIG. 8B, showing the configuration of the inwardly raised lip at the mouth of the shell of the attachment that acts as a dam to prevent outward escape of urine from the passage within the shell.

Example dimensions for a urinal attachment formed of molded silicone are set forth in the following table, referencing FIGS. 8A-8C:

TABLE A

| | |
|---|---|
| a | 4.50 in |
| b | 2.75 in |
| c | 0.06 in |
| d | 1.03 in |
| e | 0.05 in |
| f | 0.82 in |
| h | 1.50 in |
| i | 1.2 in |
| j | 0.91 in |
| k | 1.25 in |
| l | 0.50 in |
| m | 0.06 in |
| n | 0.17 in |
| o | 0.10 in |
| p | 0.10 in |
| q | R0.03 in |
| r | R0.03 in |
| s | R0.02 in |

It will be understood that the dimensions in the above table are provided by way of example rather than limitation and may vary depending on materials, shape, mounting type and other design factors.

In addition to being formed of a resiliently flexible material, the shell may be provided with additional features that enhance and/or compliment its basic functions. For example, the material of the shell may be made of or provided with liquid repelling, antimicrobial and/or scented materials. The shell may also be made or provided with a "glow-in-the-dark" material for nighttime use, or a material that changes in color in response to heat or being contacted by liquid; similarly, the shell or other parts of the attachments may be provided with graphics or other visible, structural and/or audible features to aid the child in developing aim. The material of the shell may also be clothes washer or dishwasher safe for repeated convenient cleaning; in other instances, the shell may be designed and constructed to be disposable after one or more uses. It is to therefore be recognized that these and various other alterations, modifications, and/or additions may be introduced into the constructions and arrangements of parts described above without departing from the spirit or ambit of the present invention.

What is claimed is:

1. A training urinal attachable to a bowl of a toilet, said training urinal comprising:
   a resiliently collapsible shell, comprising:
      an intake opening that receives a flow of urine from a standing child;
      a discharge opening that directs the flow of urine into a collection area of a bowl of a toilet; and
      a passage that constrains the flow of urine from said intake opening to said discharge opening; and a mounting portion attachable to said toilet so as to position said shell over an area of a rim of said bowl that is covered by a seat of said toilet when lowered;

whereby, in response to said seat of said toilet being lowered said shell of said urinal attachment compresses to a collapsed configuration between a lower side of said seat and an upper side of said rim of said bowl, and in response to said seat being raised said shell expands to an erected configuration in which said intake opening extends upwardly above said rim of said toilet to receive a flow of urine from a standing child.

2. The training urinal attachment of claim 1, wherein said resiliently collapsible shell comprises:

a shell formed of a resiliently flexible material.

3. The training urinal attachment of claim 2, wherein said shell formed of a resiliently flexible material comprises:

a shell molded unitarily of said resiliently flexible material.

4. The training urinal attachment of claim 1, wherein said passage of said resiliently collapsible shell comprises:

an inwardly and downwardly angled passage that directs said flow of urine therethrough towards said bowl of said toilet.

5. The training urinal attachment of claim 4, wherein said intake opening and said discharge opening are aligned along a line of sight through said inwardly and downwardly angled passage so that said discharge opening is visible through said intake opening for use as a target by a standing child.

6. The training urinal attachment of claim 4, wherein said resiliently collapsible shell comprises:

a generally down-curved shell having said passage therein.

7. The training urinal attachment of claim 6, wherein said generally down-curved shell comprises:

a down-curved shell having a horizontal length approximately equal to or less than a predetermined width of a ring of said seat, so that said shell is substantially covered by said ring when said seat is lowered.

8. The training urinal attachment of claim 5, wherein said inwardly and downwardly angled passage comprises:

a curved passage tapering from larger to smaller from said intake opening to said discharge opening.

9. The training urinal attachment of claim 6, wherein said resiliently collapsible shell further comprises:

an inwardly raised lip extending over at least a lower portion of a perimeter of said intake opening, that forms a dam against backflow from said flow of urine escaping said intake opening.

10. The training urinal attachment of claim 8, wherein said discharge opening comprises:

an opening at an end of said shell having a raised upper edge that provides an enlarged view into said collection area of said bowl visible through said intake opening.

11. The training urinal attachment of claim 8, wherein said resiliently collapsible shell further comprises:

a hood portion extending above said intake opening that substantially covers said intake opening when said shell is in said collapsed configuration with said seat of said toilet lowered thereon.

12. The training urinal attachment of claim 2, wherein said mounting portion attachable to said toilet comprises:

means for detachably mounting said resiliently collapsible shell to a rim of said bowl of said toilet.

13. The training urinal attachment of claim 12, wherein said means for detachably mounting said resiliently collapsible shell to said rim of said bowl of said toilet is selected from the group consisting of:

suction cups;
brackets;
clips;
magnets;
adhesives; and
combinations thereof.

14. The training urinal of claim 2, wherein said mounting portion attachable to said toilet comprises:

at least one suction cup mounted to said resiliently collapsible shell that is attachable to a rim of said bowl of said toilet.

15. The training urinal attachment of claim 14, wherein said at least one suction cup attachable to said rim of said bowl of said toilet comprises:

first and second suction cups mounted to a lower side of said resiliently collapsible shell proximate said intake and discharge openings and facing towards one another, that engage outer and inner vertical sides of said rim of said bowl of said toilet.

16. The training urinal attachment of claim 15, wherein said resiliently collapsible shell further comprises:

a depending flange portion extending downwardly proximate said intake opening so as to be located adjacent said outer vertical side of said rim of said bowl of said toilet, said depending flange having said first suction cup mounted thereon; and a lower side wall portion extending downwardly proximate said discharge opening so as to be located adjacent said inner vertical side of said rim of said bowl of said toilet, said lower side wall portion having said second suction cup mounted thereon.

17. The training urinal attachment of claim 16, wherein said resiliently collapsible shell further comprises:

a horizontally flattened bottom wall portion located intermediate said depending flange portion proximate said intake opening and said lower side portion proximate said discharge opening, that rests atop a horizontal upper side of said rim of said bowl of said toilet so as to support and stabilize said shell on said rim.

18. A training urinal attachment mountable to a bowl of a toilet, said training urinal attachment comprising:

a generally down-curved resiliently collapsible shell formed of a resiliently flexible material having a memory shape, said resiliently collapsible shell comprising:

an intake opening that receives a flow of urine from a standing child;

a discharge opening that directs said flow of urine into a collection area of a bowl of a toilet; and a tapered passage that constrains said flow of urine from said intake opening to said discharge opening;

said intake and discharge openings being aligned along a common line of sight extending at an inward and downward angle through said passage so that said discharge opening is visible through said intake opening for use as a target by a standing child;

at least first and second suction cups mounted to a lower side of said resiliently collapsible shell proximate said intake and discharge openings and facing towards one another, that engage inner and outer vertical sides of a rim of said bowl of said toilet so as to detachably mount said resiliently collapsible shell thereto; and a horizontally flattened bottom wall portion located intermediate the intake opening and the discharge opening, that rests atop a horizontal upper side of the rim of the bowl of the toilet so as to support and stabilize the shell thereon;

whereby, in response to said seat of said toilet being lowered said shell of said urinal attachment compresses to a collapsed configuration between a lower side of said seat and an upper side of said rim of said bowl, and in response to said seat being raised said shell expands to an erected configuration in which said intake opening extends upwardly above said rim of said toilet to receive a flow of urine from a standing child.

19. A method for training a standing child to urinate into a toilet, said method comprising the steps of:
providing a resiliently collapsible shell comprising:
an intake opening that receives a flow of urine from a standing child;
a discharge opening that directs said flow of urine into a collection area of a bowl of said toilet; and
a passage that constrains said flow of urine from said intake opening to said discharge opening;
mounting said resiliently collapsible shell to said toilet so that said shell is positioned over an area of a rim of said bowl that is covered by a seat of said toilet when lowered;
lowering said seat of said toilet to said rim of said bowl so that said seat compresses said resiliently collapsible shell to a collapsed configuration in an area between a lower side of said seat and an upper side of said rim of said bowl; and
raising said seat of said toilet away from said rim of said bowl so that said resiliently collapsible shell expands to an erected configuration in which said intake opening extends upwardly above said rim to receive said flow of urine from a standing child.

20. The method of claim 19, further comprising the step of:
aligning said intake opening and said discharge opening along a common line of sight extending at an inward and downward angle through said passage of said resiliently collapsible shell, so that when said resiliently collapsible shell is in said erected configuration said discharge opening is visible through said intake opening for use as a target by a standing child.

* * * * *